United States Patent [19]

Showell

[11] Patent Number: 4,853,409
[45] Date of Patent: Aug. 1, 1989

[54] 3-SUBSTITUTED-2-OXINDOLE-1-CARBOXAMIDES FOR SUPPRESSING T-CELL FUNCTION

[75] Inventor: Henry J. Showell, New London County, Conn.

[73] Assignee: Pfizer Inc., New York, N.Y.

[21] Appl. No.: 181,142

[22] Filed: Apr. 13, 1988

[51] Int. Cl.[4] .............................................. A61K 31/40
[52] U.S. Cl. .................................... 514/418; 514/414; 514/885
[58] Field of Search ........................ 514/414, 418, 885

[56] References Cited

U.S. PATENT DOCUMENTS 4,556,672 12/1985 Kadin .................................. 514/418
4,569,942  2/1986 Kadin .................................. 514/418

OTHER PUBLICATIONS

Bailey, J. M. et al., "Regulation of T-Lymphocyte Mitogenesis by the Leukocyte Product 15-Hydroxy--eicosatetraenoic Acid (15-HETE)", Cellular Immunology, 67, 112-120 (1982).
Kelly, J. P. et al., "Effect of Inhibitors of Arachidonic Acid Metabolism on Mitogenesis in Human Lymphocytes: Possible Role of Thromboxanes and Products of the Lipoxygenase Pathway", J. Immunology, 122, 1563-1571 (1979).
Leung, K. H. et al., "Modulation of the Development of Cell-Mediated Immunity: Possible Role of the Products of the Cyclo-oxygenase and the Lipoxygenase Pathways of Arachidonic Acid Metabolism", Int. J. Immunopharmac., 4, 195-204 (1982).
Crout, J. E. et al., "Suppression of Lymphocyte Transformation After Aspirin Ingestion", N.E.J. Med., 292, 221-223 (1975).
Bellanti, Joseph A., *Immunology III*, W. B. Saunders Co., Philadelphia (1985), Chapter 20, Part C, pp. 409-446.
*Autoimmunity: Basic Concepts; Systemic and Selected Organ-Specific Diseases*, Cruse, J. M. and Lewis, Jr., R. E., Eds., S. Karger, New York (1985), pp. 51-71.
Hanna, N. et al., "Cytokines: Targets for Novel Anti--Inflammatories: An Overview", Adv. Inflammation Res., vol. 12 (1988), pp. 11-14.
O'Flaherty, J. T. et al., "Neutrophil-Aggregating Activity of Monohydroxyeicosatetraenoic Acids", A.J.P., 104, 55-62 (1981).
Kunkel, S. L. et al., "Prostaglandins and the Regulation of Immune Responses", Adv. Inflammation Res., 7, 93-109 (1984).
Gordon, D. et al., "Control of Lymphokine Secretion by Prostaglandins", Nature, 262, 401-402 (1976).
Kunkel, S. L. et al., "Role of Lipoxygenase Products in Murine Pulmonary Granuloma Formation", J. Clin. Invest., 74, 514-524 (1984).
Pages 6-8 of the Presentation by Barry M. Bloom to Analysts of First Boston, New York City, New York on Sep. 10, 1987.
F-D-C Reports, Sep. 28, 1987, p. 11.
"Three Pfizer Drugs Promising; FDA Okay to Be Sought in '89", Chemical Marketing Reporter, Sep. 14, 1987, p. 7.
F-D-C Reports, Sep. 14, 1987, p. 2.

*Primary Examiner*—Douglas W. Robinson
*Assistant Examiner*—Roger Gobrogge
*Attorney, Agent, or Firm*—Peter C. Richardson; J. Trevor Lumb; Gregg C. Benson

[57] ABSTRACT

This invention relates to the use of certain 3-substituted-2-oxindole-1-carboxamides of the formula

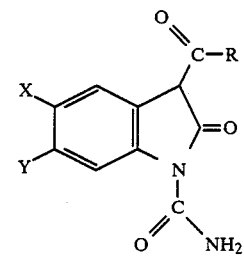

and the pharmaceutically-acceptable base salts thereof wherein X is H, Cl or F; Y is H or Cl; and R is benzyl or thienyl to suppress T-cell function in a mammal. This invention also relates to the use of such compounds for treating T-cell mediated autoimmune disorders of the systemic or organ specific type. The methods of this invention comprise administering a T-cell function suppressing amount of the compounds and salts of this invention to such a mammal.

40 Claims, No Drawings

3-SUBSTITUTED-2-OXINDOLE-1-CARBOXAMIDES FOR SUPPRESSING T-CELL FUNCTION

BACKGROUND OF THE INVENTION

1. Field of the Invention

This invention relates to the use of certain 3-substituted-2-oxindole-1-carboxamides and the pharmaceutically-acceptable base salts thereof for suppressing T-cell function in a mammal. The invention compounds and salts are useful in treating T-cell mediated autoimmune disorders. Such autoimmune disorders can be systemic or organ specific and include, but are not limited to, multiple sclerosis, systemic lupus erythematosus (SLE), type I diabetes, myasthenia gravis and chronic liver disease. The use of such compounds and salts comprise administering an effective amount thereof to a mammal.

2. General Background

Certain 3-substituted-2-oxindole-1-carboxamides of the formula

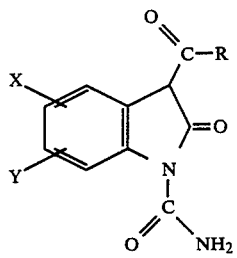

and the pharmaceutically-acceptable base salts thereof wherein, inter alia, X is H, Cl or F; Y is H or Cl; and R is benzyl or thienyl are disclosed and claimed in U.S. Pat. No. 4,556,672 which is assigned to the assignee hereof. That patent discloses that those compounds, in addition to being useful as antiinflammatory and analgesic agents. are inhibitors of both cyclooxygenase (CO) and lipoxygenase (LO). The teachings thereof are incorporated herein by reference.

Certain autoimmune disorders of the systemic and organ specific type such as type I diabetes, chronic liver disease and myasthenia gravis, among others, are described in *Autoimmunity: Basic Concepts; Systemic and Selected Organ Specific Diseases*, Cruse, J. M. and Lewis, Jr., R. E., Eds., S. Karger, New York, 1985 at pages 51-71. The role of T-cell dysfunction and certain autoimmune disorders of the systemic and organ specific type such as systemic lupus erythematosus (SLE), among others, are disclosed in Bellanti, Joseph A., Immunology III, W. B. Saunders Co., Philadelphia (1985), Chapter 20, Part C., pages 409-446. The teachings of those references are incorporated herein by reference.

In copending U.S. patent application Ser. No. 181,131 entitled 3-Substituted-2-Oxindole-1-Carboxamides As Inhibitors of Interleukin-1 Biosynthesis, filed concurrently herewith and which is assigned to the assignee hereof, it is disclosed that the compounds of this invention do not inhibit lipoxygenase in the present of serum.

It has been reported that lipoxygenase metabolites play a role in T-lymphocyte mitogenesis. Baily, J. M., et al., Cellular Immunology, 67, 112-120 (1982); and Kelly, J. P., et al., J. Immunology, 122, 1563-1571 (1979). Further, certain inhibitors of cyclooxygenase have been reported to increase cell-mediated immunity, certain lipoxygenase inhibitors have been reported to inhibit cell-mediated immunity and certain cyclooxygenase and lipoxygenase inhibitors have been found to enhance cell-mediate immunity at lower concentrations and inhibit such immunity at higher concentrations. Leung, K. H., et al., Int. J. Immunopharmac., 4, 195-204 (1982).

Aspirin has been reported to suppress blastogenesis of lymphocytes. Crout, J. E., et al., N. E. J. Med., 292, 221-223 (1975). Further, IL-1 has been reported to augment T-cell activation and lymphokine release. See, Hanna, N. and Wood D. D., Adv. Inflammation Res., Vol. 12 (1988) at 11-14 and reference cited therein.

Until the invention herein, there was no report of use or intent to use the compounds or salts of this invention to suppress T-cell function independent of lipoxygenase inhibition and to treat T-cell mediated autoimmune disorders with such compounds nor any appreciation of their role in such treatments.

SUMMARY OF THE INVENTION

It has been found that certain 3-substituted-2oxindole-1-carboxamides of the formula

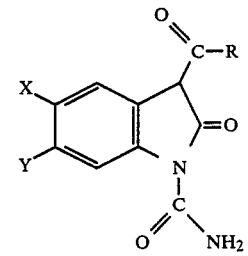

and the pharmaceutically-acceptable base salts thereof wherein X is H, Cl or F; Y is H or Cl; and R is benzyl or thienyl suppress T-cell function independent of their lipoxygenase inhibiting activity and, thus, are useful in treating T-cell mediated autoimmune disorders. Such autoimmune disorders can be systemic or organ specific and include, but are not limited to, multiple sclerosis, systemic lupus erythematosus (SLE), type I diabetes, myasthenia gravis and chronic liver disease.

The methods of using the compounds and their pharmaceutically-acceptable base salts comprise administering to a mammal an effective amount of such compounds. Administration can comprise any known method for therapeutically providing a compound to a mammal such as by oral or parenteral administration as defined hereinbelow.

DETAILED DESCRIPTION OF THE INVENTION

The compounds of this invention which are of the formula

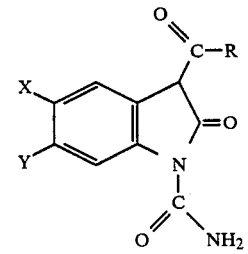

and the pharmaceutically-acceptable base salts thereof wherein X is H, Cl or F; Y is H or Cl; and R is benzyl or thienyl and the preparation thereof are disclosed in U.S. Pat. No. 4,556,672, the teachings of which are incorporated herein by reference. This invention concerns new uses for such compounds which comprise methods for suppressing T-cell function in a mammal independent of inhibition of lipoxygenase. Also within the scope of this invention are methods of treating T-cell mediated autoimmune disorders which can be either systemic or organ specific.

Of the methods described above, preferred therein are those where the compound employed is of the formula above wherein X is Cl, Y is H and R is thienyl; those wherein said compound X is F, Y is Cl and R is thienyl; those wherein in said compound X is F, Y is Cl and R is 2-thienyl and those wherein in said compound X is H, Y is Cl and R is benzyl. Particularly preferred are methods wherein said compound X is Cl, Y is H and R is 2-thienyl.

As disclosed in U.S. Pat. No. 4,556,672, the compounds of this invention hereinabove described are acidic and form base salts. All such base salts are within the scope of this invention and can be formed as taught by that patent. Such suitable salts, within the scope of this invention, include both the organic and inorganic types and include, but are not limited to, the salts formed with ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of bases which form such base salts include ammonia, primary amines, such as n-propylamine, n-butylamine, aniline, cyclohexylamine, benzylamine, p-toluidine, ethanoline and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides such as sodium ethoxide and potassium methoxide; hydrides such as calcium hydride and sodium hydride; and carbonates such as potassium carbonate and sodium carbonate. Preferred salts are those of sodium, potassium, ammonium, ethanolamine, diethanolamine and triethanolamine. Particularly preferred are the sodium salts.

Also within the scope of this invention are the solvates such as the hemihydrates and monohydrates of the compounds hereinabove described.

The method of this invention comprise administering the invention compounds and the pharmaceutically-acceptable base salts thereof to a mammal. Such compounds and their salts can be administered to said mammal either alone or, preferably, in combination with pharmaceutically-acceptable carriers or diluents in a pharmaceutical composition, according to standard pharmaceutical practice. Such administration can be oral or parenteral. Parenteral administration as used herein includes, but is not limited to, intravenous, intramuscular, intraperitoneal, subcutaneous, transdermal and topical administration. However, while it is generally preferred to administer such compounds and their salts orally, parenteral administration may be preferable in treating certain disorders such as chronic liver disease.

In general, these compounds and their salts are most desirably administered in doses ranging from about 40 mg up to about 200 mg per day for oral administration and from about 1 mg up to about 200 mg per day for parenteral administration, although variations will still necessarily occur depending upon the weight of the subject being treated. The appropriate dose for suppressing T-cell function in a mammal and for treatment of T-cell mediated autoimmune disorders with the compounds and their salts of this invention will be readily determined by those skilled in the art of prescribing and/or administering such compounds. Nevertheless, it is still to be appreciated that other variations may also occur in this respect, depending upon the species of mammal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur, provided that such higher dose levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato to tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hardfilled gelatin capsules; preferred materials in this connection also include, by way of example and not of limitation, lactose or milk sugar as well as high molecular weight polyethylene glycols. When aqueous suspension and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the preferred mode of administration of the compounds of this invention or their pharmaceutically-acceptable base salts is oral, they may be administered parenterally as well.

For purposes of parenteral administration, solutions of these particular compounds in sesame or peanut oil or in aqueous propylene glycol may be employed, as well as sterile aqueous solutions of the corresponding water soluble base salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. Needless to say, the necessary steps should be taken throughout the preparation of these injectable solutions to insure that the final products are obtained in a sterile condition. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gelproducing materials, mineral oil, emulsifying agents, benzyl alcohol and the like. Specific transdermal flux enhancing compositions are disclosed in pending U.S. patent application Ser. No. 925,641, filed Oct. 31, 1986, which is assigned to the assignee of this invention, the teachings of which are incorporated herein by reference. For purposes of topical administration, the dosage form of the particular compound may include, by way of example and not of limitation, solutions, lotions, ointments, creams and gels.

The ability of the compounds to suppress T-cell function is demonstrated by the procedures of Kunkel, S. L., et al., J. Clin. Invest., 74, 514–524 (1984) which is described below.

Female CBA/J mice (The Jackson Laboratory, Bar Harbor, Maine) are maintained under standard care and given food and water ad libitum. Eggs are isolated from the livers of mice which have been previously infected with 200 cercariae of *Schistosome mansoni* by the method of Coker and von Lichtenberg, Proc. Soc. Exp. Biol. Med., 92, 359–364 (1956). The isolated schistosome eggs are suspended to 4,000/ml in sterile physiological saline and induction of pulmonary egg granulomas is accomplished vial tail vein injection of 2000 eggs per mouse. The compound under study is administered daily to the mouse via intraperitoneal injection after egg embolization. Dosages range from 0 to 100 mg/kg in an appropriate solvent. Mice are killed at 4, 8 and 16 days post egg challenge and the lungs are inflated with 10% buffered formalin, removed prepared for histological section and stained with hematoxylin and eosin. The pulmonary granuloma areas are measured from sections using an Omicron alpha image analyzer (Bausch and Lomb Inc., Rochester, N.Y.) with the data being fed into an attached computer. A minimum of 20 granulomas are measured from each lung and the granulomas from at least five mice per compound/dosage are measured.

What is claimed is:

1. A method of suppressing T-cell function in a mammal which comprises administering to a mammal in need thereof a T-cell function suppressing amount of a compound of the formula

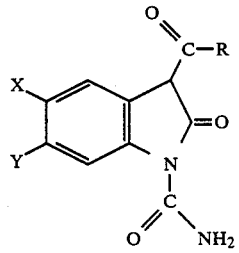

or a pharmaceutically-acceptable base salt thereof, wherein X is H, Cl or F; Y is H or Cl; and R is benzyl or thienyl.

2. The method according to claim 1 wherein X is Cl; Y is H; and R is thienyl.
3. The method according to claim 2 wherein R is 2-thienyl.
4. The method according to claim 3 wherein the pharmaceutically-acceptable base salt is sodium.
5. The method according to claim 1 wherein X is F; Y is Cl and R is thienyl.
6. The method according to claim 5 wherein R is 2-thienyl.
7. The method according to claim 1 wherein X is H; Y is Cl; and R is benzyl.
8. The method according to claim 1 wherein the compound or a pharmaceutically-acceptable base salt thereof is administered orally.
9. The method according to claim 1 wherein the compound or a pharmaceutically-acceptable base salt thereof is administered parenterally.
10. A method of treating T-cell mediated autoimmune disorders in a mammal which comprises administering to said mammal a T-cell mediated autoimmune disorder treating amount of a compound of the formula

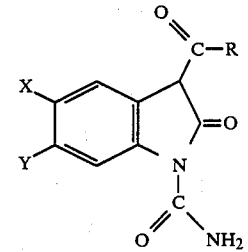

or a pharmaceutically-acceptable base salt thereof, wherein X is H, Cl or F; Y is H or Cl; and R is benzyl or thienyl.

11. The method according to claim 10 wherein X is Cl; Y is H; and R is thienyl.
12. The method according to claim 11 wherein R is 2-thienyl.
13. The method according to claim 12 wherein the pharmaceutically-acceptable base salt is sodium.
14. The method according to claim 10 wherein X is F; Y is Cl and R is thienyl.
15. The method according to claim 14 wherein R is 2-thienyl.
16. The method according to claim 10 wherein X is H; Y is Cl; and R is benzyl.
17. The method according to claim 10 wherein the compound or a pharmaceutically-acceptable base salt thereof is administered orally.
18. The method according to claim 10 wherein the compound or a pharmaceutically-acceptable base salt thereof is administered parenterally.
19. The method of treating T-cell mediated systemic autoimmune disorders in a mammal which comprises administering to said mammal a T-cell mediated systemic autoimmune disorder treating amount of a compound of the formula

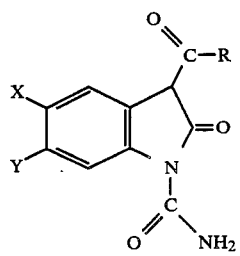

or a pharmaceutically-acceptable base salt thereof, wherein X is H, Cl or F; Y is H or Cl; and R is benzyl or thienyl.

20. The method according to claim 19 wherein X is Cl; Y is H; and R is thienyl.

21. The method according to claim 20 wherein R is 2-thienyl.

22. The method according to claim 21 wherein the pharmaceutically-acceptable base salt is sodium.

23. The method according to claim 19 wherein X is F; Y is Cl; and R is thienyl.

24. The method according to claim 23 wherein R is 2-thienyl.

25. The method according to claim 19 wherein X is H; Y is Cl; and R is benzyl.

26. The method according to claim 19 wherein the compound or a pharmaceutically-acceptable base salt thereof is administered orally.

27. The method according to claim 19 wherein the compound or a pharmaceutically-acceptable base salt thereof is administered parenterally.

28. The method according to claim 19 wherein the systemic autoimmune disorder is multiple sclerosis or systemic lupus erythematosus.

29. The method according to claim 22 wherein the systemic autoimmune disorder is multiple schlerosis or systemic lupus erythematosus.

30. A method of treating T-cell mediated organ specific autoimmune disorders in a mammal which comprises administering to said mammal a T-cell mediated organ specific autoimmune disorder treating amount of a compound of the formula

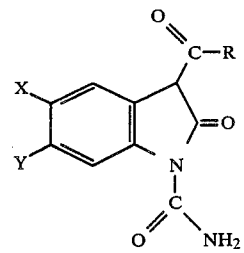

or a pharmaceutically-acceptable base salt thereof, wherein X is H, Cl or F; Y is H or Cl; and R is benzyl or thienyl.

31. The method according to claim 20 wherein X is Cl; Y is H; and R is thienyl.

32. The method according to claim 22 wherein R is 2-thienyl.

33. The method according to claim 32 wherein the pharmaceutically-acceptable base salt is sodium.

34. The method according to claim 30 wherein X is F; Y is Cl; and R is thienyl.

35. The method according to claim 34 wherein R is 2-thienyl.

36. The method according to claim 30 wherein X is H; Y is Cl; and R is benzyl.

37. The method according to claim 30 wherein the compound or a pharmaceutically-acceptable base salt thereof is administered orally.

38. The method according to claim 30 wherein the compound or a pharmaceutically-acceptable base salt thereof is administered parenterally.

39. The method according to claim 30 wherein the organ specific autoimmune disorder is type I diabetes, myasthenia gravis or chronic liver disease.

40. The method according to claim 33 wherein the organ specific autoimmune disorder is type I diabetes, myasthenia gravis or chronic liver disease.

* * * * *

UNITED STATES PATENT AND TRADEMARK OFFICE
CERTIFICATE OF CORRECTION

PATENT NO. : 4,853,409

DATED : August 1, 1989

INVENTOR(S) : Henry J. Showell

It is certified that error appears in the above-identified patent and that said Letters Patent is hereby corrected as shown below:

Column 8, line 18, "claim 20" should read -- claim 30 --; and

Column 8, line 20, "claim 22" should read -- claim 31 --.

Signed and Sealed this

Third Day of July, 1990

*Attest:*

HARRY F. MANBECK, JR.

*Attesting Officer*      *Commissioner of Patents and Trademarks*